Figure 1:
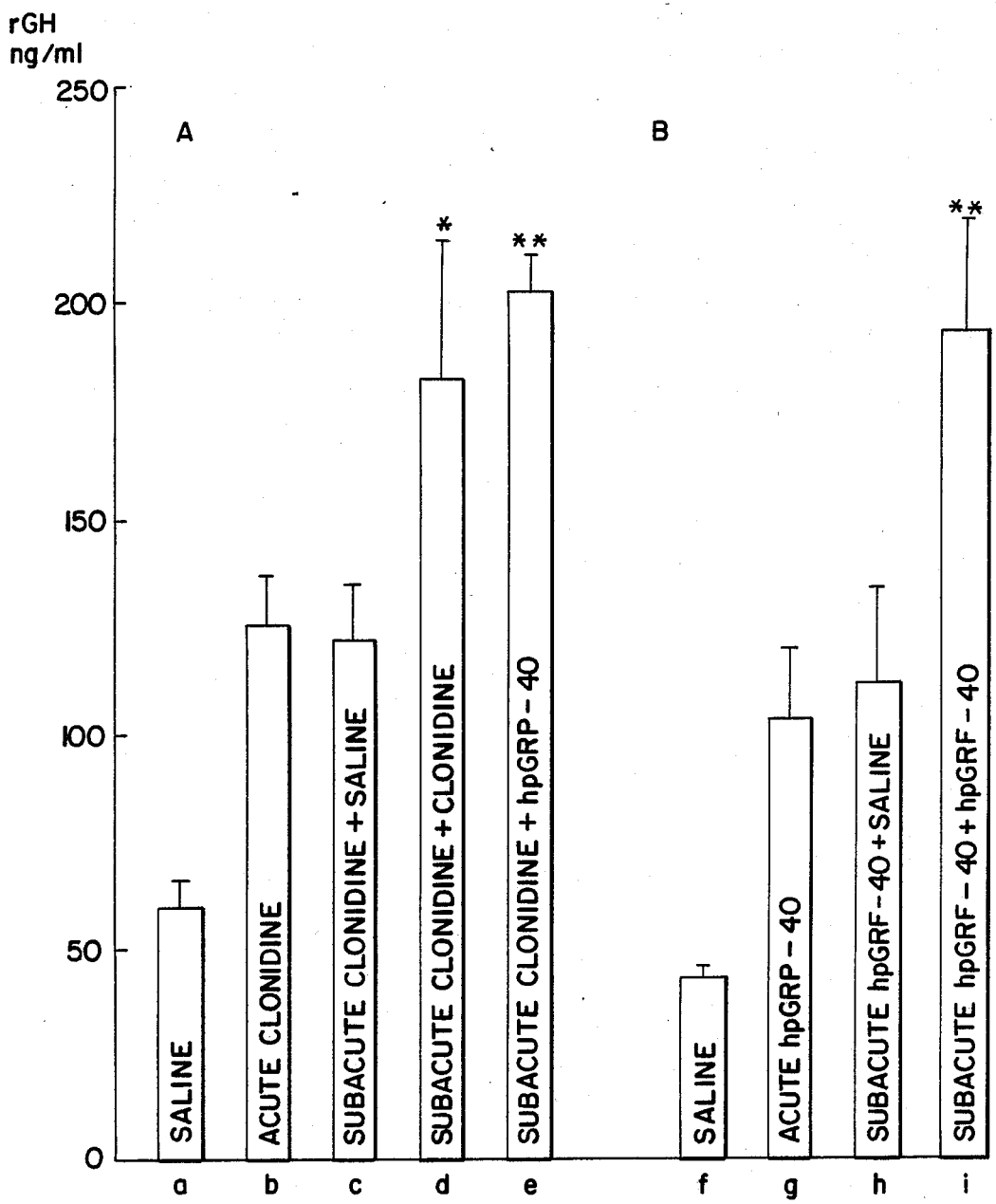

United States Patent [19]

Müller

[11] Patent Number: 4,910,215

[45] Date of Patent: Mar. 20, 1990

[54] PHARMACEUTICAL FORMULATIONS DESIGNED TO STIMULATE THE RELEASE OF SOMATOTROPIC HORMONE

[76] Inventor: Eugenio Müller, Via Mangiagalli 5, Milano 20133, Italy

[21] Appl. No.: 180,512

[22] Filed: Apr. 12, 1988

Related U.S. Application Data

[63] Continuation of Ser. No. 857,884, Apr. 30, 1986, abandoned.

[30] Foreign Application Priority Data

May 15, 1985 [IT] Italy ................. 20712 A/85

[51] Int. Cl.⁴ ............................ A61K 31/415
[52] U.S. Cl. ..................................... 514/401
[58] Field of Search .......................... 514/401

[56] References Cited

PUBLICATIONS

Lal et al., *J. Clin. Endocrinol Metab.* 1975, 41, 703–708.
Guillemin et al., *Science* 1982, 218, 585–587.
Rivier et al., *Nature* 1982, 300, 276–278.
Miki et al., *Endocrinology* 1984, 114, 1950–1952.
Katakami et al., *Neuroendocrinology* 1984, 138, 1–5.
Kashio et al., *J. Clin. Endocrinol. Metab.* 1985, 60, 396–398.
Leckman et al., *J. Am. Child Psychiatry* 1984 23(2), 174–81.
Keller et al., *Exp. Clin. Endocrinol.* 1983, 81(3), 315–320.
Pintor et al., *J. Endocrinal Invest.* 1984, 7, 253–56.
Gil-Ad et al., in Lancet 1979, 2 (8-137), 278–80.
Honor et al., in Psychoneuroendocrinology 1984, 9(3), 279–84.
Gil-Ad et al., in Isr. J. Med. Sci. 1985, 27(7) 601–4.
Maura et al., European Journal of Pharmacology; 112 (1985) 105–110.
Eriksson et al., Psychopharmacology 77 (1982) 327–331.
Falkner et al., J. Clin. Pharmacol. 21 (1981) 31–36.

*Primary Examiner*—Stanley J. Friedman
*Attorney, Agent, or Firm*—David E. Frankhouser; Alan R. Stempel; Mary-Ellen M. Timbers

[57] ABSTRACT

The use of 2,6-dichlorophenyl compounds as active principles in pharmaceutical formulations designed to stimulate the secretion or release of somatotropic hormone in man and animals is described.

5 Claims, 3 Drawing Sheets

PHARMACEUTICAL FORMULATIONS DESIGNED TO STIMULATE THE RELEASE OF SOMATOTROPIC HORMONE

This is a continuation of application Ser. No. 857,884, filed Apr. 30, 1986, now abandoned.

The present invention relates to the use of $\alpha_2$-agonists in the treatment of growth disorders due to a defective secretion of growth hormone or somatotropin. It relates in particular to the use of 2,6-dichlorophenyl compounds in pharmaceutical formulations designed to stimulate or encourage the secretion or release of the growth hormone in man and animals.

It is known that certain 2,6-dichlorophenyl compounds, such as 2-[(2,6-dichlorophenyl)amino]-2-imidazoline (known as clonidine), 2-[(2,6-dichlorophenyl)methylene]hydrazinocarboximidamide (known as guanabenz), (2,6-dichlorophenylacetyl)-guanidine (known as guanfacine), [2-[(2,6-dichlorophenyl)amino]-ethyl]-guanidine (known as guanclofine) and 1-[(2,6-dichlorophenyl)methylene amino]-3-hydroxyguanidine (known as guanoxabenz) have an antihypertensive effect and are used as such since they are able to activate the $\alpha_2$-adrenergic receptors.

The recent availability of synthetic peptide analogues isolated from human pancreatic tumours and having a powerful and specific releasing effect on the somatotropic hormone (GH) in both animals and man has provided powerful aids for the diagnosis and treatment of growth disorders. In particular, these peptide analogues, known in short as hpGRF, whose structural formula corresponds to that of the factor which releases the growth hormone (GRF) present in the human hypothalamus, appear suitable to stimulate the synthesis and release of GH in children whose secretion of the hormone is defective, since the defective GH regulation in the majority of such patients has been traced to incorrect synthesis and/or release of GRF in the hypothalamus rather than to a primitive deficiency of the hypophyseal cells which produce GH.

Control of GH secretion is very complex, since it involves hypothalamic neurohormones with a stimulating (GRF or somatocrinin) and inhibiting (somatostatin) effect as well as hypothalamic neurotransmitters and suprahypothalamic neurotransmitters. The catecholamines, particularly noradrenaline (NA) and adrenaline (A) play an important role in both man and animals amongst neurotransmitters, whose task is to regulate the secretion of GRF and samotostatin by stimulation or inhibition.

In rats, dogs and other species of animals the administration of drugs which inhibit the synthesis of NA or A, or reserpine, a drug which depletes the catecholamines, suppresses the secretion of GH. On the other hand, the administration of drugs which stimulate the $\alpha$-adrenergic receptors stimulates the release of GH. This is not only the case for rodents and animals of lower species, but also for man.

The $\alpha$-adrenergic receptors may be sub-divided, chiefly on a pharmacological basis, into the sub-types $\alpha 1$- and $\alpha 2$-adrenergic receptors. The $\alpha 1$-adrenergic receptors are activated by drugs such as methoxamine and phenylephrine and blocked by drugs such as phenoxybenzamine and prazosin; the $\alpha 2$-adrenergic receptors are activated by drugs such as clonidine and its related substances guanfacine, guanabenz etc., and blocked by drugs such as piperoxan and yohimbine.

Although clonidine stimulates the $\alpha 1$-adrenergic receptors as well as the $\alpha 2$-adrenergic receptors, recent studies have shown that its GH releasing effect is due to an $\alpha 2$-adrenergic stimulation, since it may be blocked by drugs such as yohimbine but not by prazosin. A neuroactive drug which causes the release of GH may achieve this effect either by inhibiting the secretion of somatostatin, the inhibitory peptide, or by stimulating the secretion of GRF, the stimulatory peptide, or by both these mechanisms.

It has recently been possible to demonstrate that clonidine stimulates the secretion of GH in rats pretreated with an antisomatostatin-antiserum. This observation would appear to show that the $\alpha$-adrenergic effect which the drug exerts on GH secretion is mediated not by inhibiting the release of somatostatin but rather by stimulating the release of GRF. Clonidine is, in effect, unable to stimulate the release of GH both in rats with experimentally induced lesions of the hypothalamus and in vitro by hypophyseal cells placed in culture.

This has very important implications since it would appear to indicate that clonidine and its related substances are potential GRFs, when the neurohormone is present in the hypothalamus, but its adrenergic release mechanism has been impaired. The studies mentioned above in which hpGRF was used to treat patients suffering from defective GH secretion (hypophyseal dwarfism) have shown that most of these patients had a secretory response to the stimulus, even through this was smaller in size than that of normal control subjects. These results show that the secretory defect is not primarily attributable to GH producing hypophyseal cells, but rather to the synthesis and/or release of GRF in the hypothalamus. It could therefore be supposed, at least in some of these cases, that the defect was not in the synthesis but in the release of GRF as a result of a lack of neurotransmitters, for example catecholaminergic transmitters, operating functionally upstream of the GRF system.

It has recently been hypothesised that children who are of small height, with an annual speed of growth of 4 cm or less, a bone age 2 or more years behind their chronological age, and a clear decrease in daily GH secretion, despite the presence of a normal somatotropic response to pharmacological GH-releasing stimuli, have a neurotransmitter defect of this type in their central nervous system.

On the basis of these assumptions, drugs such as the above-mentioned 2,6-dichlorophenyl compounds which are able to activate adrenergic neurotransmission and consequently to cause the release of GRF from the hypothalamus with a subsequent hypophyseal stimulation of GH secretion, could provide an effective treatment for patients suffering from defective GH secretion.

The present invention will now be illustrated in more detail with reference to a series of tests carried out with clonidine, from which experimental results were obtained from laboratory animals (newborn rats) and children with growth disorders.

EXAMPLE 1

The effect of clonidine on somatotropic hormone levels in young rats.

Forty rats, five-day-old, divided into 5 groups of 8 animals each. The rats of three groups received 150 $\mu$g/kg of clonidine administered subcutaneously twice daily for 5 days. On the tenth day, and 14 hours after the final injection, the rats of the three groups treated in this way received a single injection of physiological solution, clonidine (150 μg/kg) or hpGRF (20 ng/100 g) respectively, whilst the rats of the other two non-treated groups received a single injection of physiological solution or clonidine (150 μg/kg) respectively. Fifteen minutes after the final injection the rats of all the groups were killed by decapitation and their blood and hypophysis were removed for radioimmunological measurement of the somatotropic hormone.

At the same time 32 five-day-old rats were divided into 4 groups of 8 animals each. The animals of two groups were respectively treated with 20 ng/100 g of hpGRF administered subcutaneously twice daily for 5 days. On the tenth day and 14 hours after the final injection, the rats of these two groups received a single injection of physiological solution and hpGRF (20 ng/100 g) respectively, whilst the rats of the other two non-treated groups received, again on the 10th day, an injection of physiological solution and hpGRF (20 ng/100 g) respectively. The rats were also killed in this case by decapitation 15 minutes after the final injection and their blood and hypophysis were removed for radioimmunological measurement of the somatotropic hormone.

As a further control, a further group of 11 five-day-old rats received injections of physiological solution twice daily for 5 days and also received a further single injection of physiological solution on the 10th day 14 hours after the final injection.

The amounts of physiological solution injected were equivalent in volume to the amounts of active principle in all cases.

The results obtained are summarised in the form of averages in FIG. 1 attached, whilst the following Table 1 gives by way of comparison the average hypophyseal content of somatotropic hormone in a certain number of 10-day-old rats previously treated for five days with physiological solution, clonidine and hpGRF respectively as described above and finally treated with single injections of physiological solution.

TABLE 1

| No. of Rats | Treated with | Hypophyseal GH content (μg/mg prot.) |
| --- | --- | --- |
| 11 | Physiol. sol. + physiol. sol. | 104.5 ± 17.4 |
| 5 | Clonidine + physiol. sol. | 243.2 ± 21.1* |
| 7 | hpGRF + physiol. sol. | 183.4 ± 27.5 |

*p < 0.01 vs. physiological solution + physiological solution (Dunnett t test)

As can be seen from the results obtained and shown in diagram form in FIG. 1 for 10-day-old rats, the single injection of clonidine caused a marked increase in the plasma levels of GH (b), whilst the prolonged administration of clonidine to 5-day-old rats caused a protracted increase in basal plasma levels of GH (c). In the case of rats treated with clonidine for 5 days, the acute stimulus caused by the final subsequent injection of the drug further increased the basal plasma levels of GH (d). The final administration of hpGRF to 10-day-old rats pretreated for 5 days with clonidine caused an effect (e) which may be superimposed on the effect of the acute administration of clonidine (d). Moreover, as shown in Table 1, the hypophyseal GH content of the rats injected with clonidine for 5 days was significantly higher than that of the rats treated exclusively with physiological solution.

These results show that the acute administration of clonidine causes a marked increase in plasma levels of GH in young rats and that the same effect is induced in newborn animals by treatment with clonidine for five days.

Since the mean biological life of clonidine has been calculated to be fewhours in man, the effect of the subacute administration of clonidine on plasma concentrations of GH, evaluated 14 hours after the final dose of clonidine, shows the ability of the drug in question to cause an increase in the synthesis and release of GH. This is borne out by the observation that these rats had a higher hypophyseal GH content than the rats treated with physiological solution and that a further single dose of clonidine induced a higher increase in the plasma content of GH than that induced in the control rats. This provides clear experimental evidence that the hypophyseal availability of GH, and therefore the quantity of hormone which may be released, is increased by treatment with clonidine.

Parallel tests using the neuropeptide show that the effect of clonidine may, in the test conditions described above, be to release endogenous GR. As FIG. 1 shows, the prolonged administration of hpGRF to 5-day-old rats caused a marketed increase in the plasma levels of GH (h), and the sub-acute administration of hpGRF did not attenuate the GH-releasing effect of a further single dose of the peptide (i).

In this case as well the hypophyseal GH content of rats receiving hpGRF for 5 days was significantly higher than that of the rats which received only physiological solution (Table 1).

EXAMPLE 2

Effects of the oral administration of clonidine on children with growth disorders.

TABLE 2

| Patient | Sex | Age (years) Chronol. | Bone age* | Percentile | Growth speed (cm/year) | Puberal Stage (Tanner) | Height (cm) |
| --- | --- | --- | --- | --- | --- | --- | --- |
| (with IGHD) | | | | | | | |
| M.C. | M | 11 10/12 | 9 9/12 | <3 | 2.7 | $P_0$ | 119.0 |
| F.V. | M | 12 0/12 | 9 9/12 | <3 | 2.1 | $P_0$ | 121.0 |
| C.M. | M | 12 1/12 | 10 4/12 | <3 | 4.7 | $P_0$ | 121.5 |
| T.G. | M | 12 4/12 | 10 6/12 | <3 | 4.0 | $P_0$ | 132.0 |
| (with CGD) | | | | | | | |
| B.L. | F | 5 10/12 | 5 2/12 | <3 | 5.1 | $P_0$ | 96.5 |
| L.M. | F | 12 3/12 | 9 9/12 | <3 | 4.8 | $P_0$ | 111.7 |
| L.N. | M | 14 0/12 | 12 1/12 | <3 | 4.5 | $P_2$ | 134.0 |
| R.F. | M | 7 7/12 | 6 2/12 | <3 | 4.0 | $P_0$ | 109.5 |

*Calculated using the T.W. 2 method of Tanner

Eight patients were studied, four males affected by isolated growth hormone deficiency (IGHD) and two males and two females suffering from constitutional growth delay (CGD). The clinical symptoms of these patients are summarised in Table 2.

In the case of the children with IGHD, the GH deficiency was detected by at least two stimulation tests with insulin and clonidine and was diagnosed as "isolated" when other functional tests for hypophyseal activity, including evaluation of gonadotropin secretion (LH-RH test), ACTH secretion (insulin hypoglycaemia) and TSH and prolactin secretion, proved normal. None of these children had previously been treated with a somatotropin replacement therapy.

A daily dosage of 0.1 mg/m$^2$ of body surface of Clonidine (Catapresan of Boehringer Ingelheim) was administered orally in two daily doses (0.033 mg/m$^2$ at 8 AM and 0.066 mg/m$^2$ before sleep) to all the children in question. The basal plasma levels of GH and somatomed in C (SM-C), an important biological indicator of somatotropic activity, were measured before commencing treatment with clonidine and 15, 30, 45 and 60 days after treatment had commenced. Acute stimulation tests with hpGRF and clonidine were also carried out before treatment and at the end of the first 60 days of treatment with clonidine. The GH and SM-C evaluations and the stimulation tests with hpGRF and clonidine were carried out 14 hours after the final dose of clonidine.

GH levels were determined using reagents supplied by CEA-IRE Sorin of Saluggia. Haematic levels of SM-C were determined using reagents supplied by the Nichols Institute Diagnostic of S. Juan Capistrano, Calif., USA. Plasma levels of gonadotropin and prolactin (Biodata, Milan), TSH (Radim, Rome), hydrocortisone (DEA-IRE Sorin, Saluggia) and serum glucose (Boehringer) were evaluated after 15, 30, 45 and 60 days of treatment by radioimmunological or enzymatic measurement. Heart rate and arterial pressure were measured with the patients supine, at the same time intervals as during the acute test with clonidine, and subjective and objective side effects were recorded. Conventional laboratory tests were carried out periodically.

Figure 2:
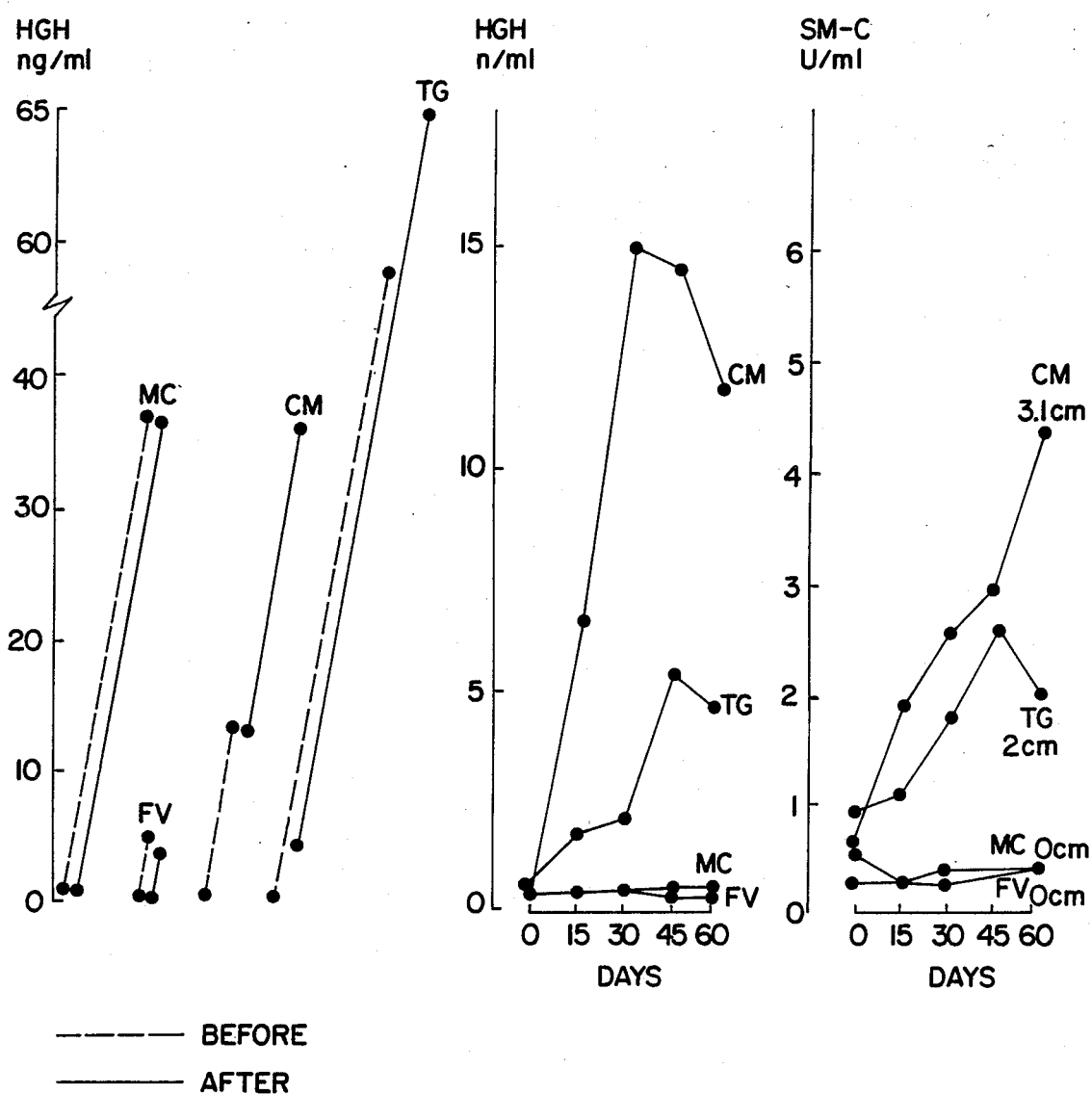
Figure 3:
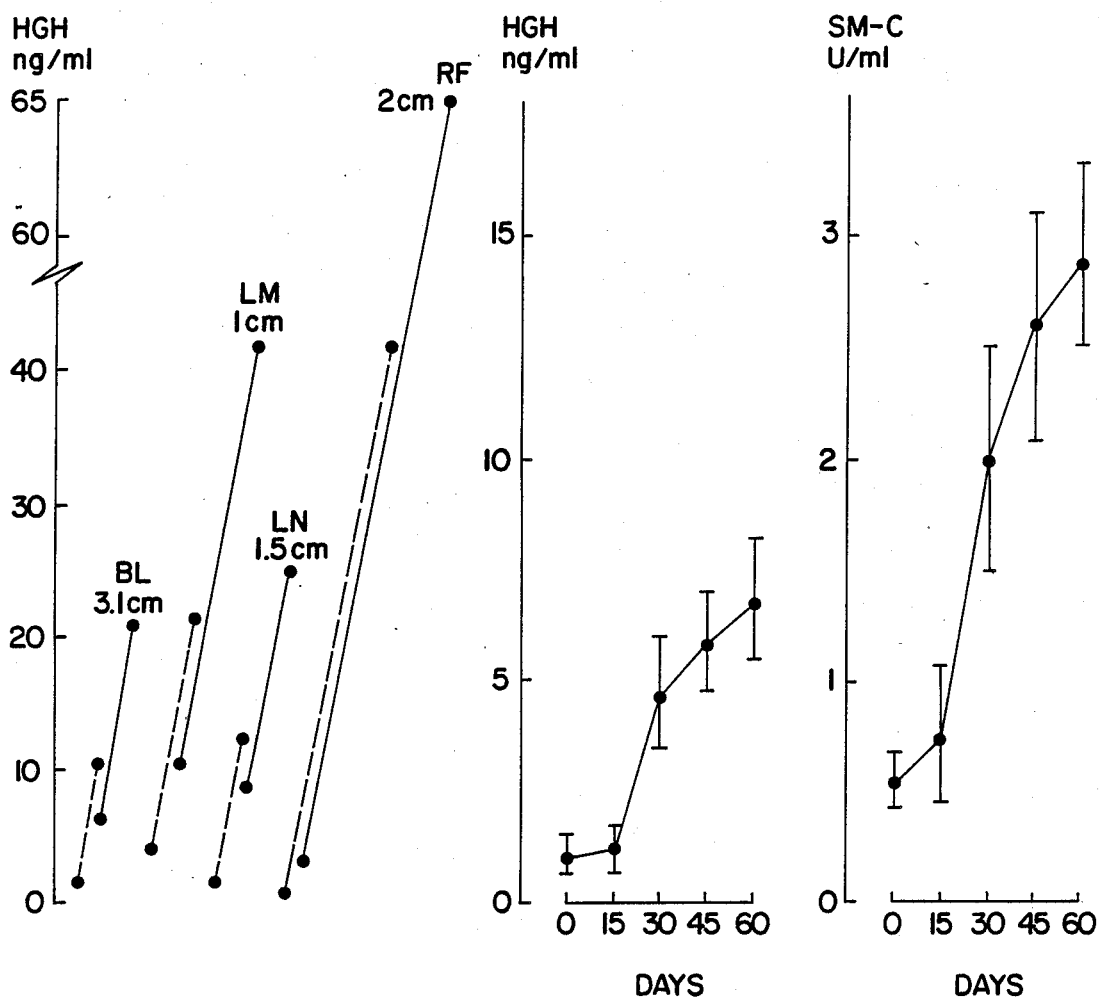

The results obtained are shown schematically in FIG. 2 for the children with IGHD and in FIG. 3 for the children with CGD. In both Figures, the left-hand graph shows the maximum plasma level of GH recorded before and after two months of treatment with clonidine, while the central graph and the right-hand graph show basal levels of GH and serum levels of SM-C respectively. Increases in linear growth over the 2-month period are shown in brackets.

As can be seen from FIG. 2, a 60-day treatment with clonidine led, in the case of two of the children with IGHD (C.M., T.G.) considered to be responsive, to a very marked increase in basal levels of GH and SM-C, increased the hypophyseal response to hpGRF and stimulated linear growth (CM: 4.7 cm/year before, 18.6 cm/year after; TG: 4.0 cm/year before, 12.0 cm/year after). The somatotropic response after the acute administration of clonidine to these children also increased after the treatment. In the case of patient C.M. the peak somatotropic response to the acute test with clonidine was 4.3 ng/ml (180 mins.) and 21.0 ng/ml (30 mins.) before and after 60 days of treatment respectively; in the case of patient T.G., the corresponding values were 1.8 ng/ml (60 mins.) and 8.0 ng/ml (120 mins.). In contrast, none of the above parameters were changed by the administration of clonidine in the case of patients M.C. and F.V. In the case of patient M.C. the peak somatotropic response to the acute test with clonidine was 2.6 ng/ml (30 mins.) before the treatment and 3.9 ng/ml (90 mins.) after the treatment; in the case of patient F.V. the corresponding values were respectively 1.9 ng/ml (60 mins.) and 3.5 ng/ml (30 mins.). It should be noted in the case of patient M.C. that a very marked response to hpGRF coupled with a persistent lack of response to clonidine stimulation showed the existence of a primitive defect in hypothalamic GRF function.

As can be seen from FIG. 3, the basal levels of GH and SM-C and the hypophyseal response to hpGRF increased and linear growth was accelerated (B.L. 5.1 cm/year before, 18.6 cm/year after; L.M. 4.8 cm/year before, 6.0 cm/year after; L.N. 4.5 cm/year before, 9.0 cm/year after; R.F. 4.0 cm/year before, 12.0 cm/year after) in all the children with CGD treated with clonidine. In the case of patients B.L., L.M., L.N. and R.F. the peak somatotropic response to the acute test with clonidine before treatment was 8.0 ng/ml (90 mins.), 5.4 ng/ml (30 mins.), 6.8 ng/ml (60 mins.) and 13.5 ng/ml (60 mins.) respectively, whereas these values were 19.0 ng/ml (150 mins.), 17.0 ng/ml (15 mins.), 16.4 ng/ml (30 mins.) and 17.6 ng/ml (45 mins.) respectively after the treatment.

None of the children showed undesirable side effects during the treatment with clonidine, while the acute treatment caused drowsiness or sleep and a slight reduction of systolic pressure (approximately 20 mmHg) both before and after the chronic treatment with clonidine. The drug did not impair basal plasma levels of TSH, gonadotropin, prolactin and glucose. A reduction of the plasma levels of hydrocortisone took place in all the patients during the acute test with clonidine both in the period preceding the treatment and in the period after the treatment. No significant differences in hydrocortisone plasma levels were observed with respect to basal levels during the treatment. Conventional laboratory tests remained unchanged for all the patients during the chronic treatment with clonidine.

The preliminary studies reported above prompted a new series of investigations with clonidine in a larger number of children. In these studies only subjects affected by constitutional delay of growth were studied. Forty subjects whose clinical characteristics are reported in Table 3, underwent investigation. As in the previous experiments they underwent administration of clonidine (100/μg/m$^2$ p.o., daily) and were checked for peak plasma GH response to GHRH (GRF1-40, 1/μg/kg, i.v.) and clonidine (150/μg/m$^2$ p.o.), basal SM-C, and growth velocity (GV), before and at 2 and 4 months of clonidine treatment. Children were considered "responsive" to clonidine (C-R) when the pretreatment GV rose from <4 cm/yr. to >6 cm/yr and/or doubled the basal value. On this basis 21/40 children at 2 months (11 males and 10 females, Nos. 1, 3, 5, 9, 10, 11, 12, 14, 15, 16, 17, 18, 20, 21, 23, 24, 25, 28, 32, 36 and 37). and 21/37 children (15 males and 6 females, (Nos. 1, 5, 6, 10, 11, 12, 13, 14, 15, 16, 20, 21, 22, 23, 24, 27, 30, 31, 32, 37 and 40) at 4 months were C-R (Table 4). In particular in the C-R children, mean pretreatment values:peak response to GHRH, 25.2±4.8 ng/ml; peak response to clonidine, 16.5±5.0 ng/ml; SM-C, 1.8±0.3 U/ml; GV, 2.8±0.2 cm/yr, rose after 2 months of clonidine to 43.6±6.0 ng/ml; 30.8±5.0 ng/ml; 2.8±0.2 U/ml; 7.4±0.4 cm/yr, respectively. After 4 months of clonidine treatment they were as follows: 46.7±4.0 ng/ml; 24.7±2.5 ng/ml; 2.38±0.3 U/ml; 7.8±0.4 cm/yr, respectively from pre-treatment values of 31.7±7.9 ng/ml; 11.7±2.0 ng/ml; 1.4±0.1 U/ml; 2.8±0.2 cm/yr.

In the non-responsive children (C-NR) (11 males and 8 females at 2 months, (Nos. 2, 4, 6, 7, 8, 13, 19, 22, 26, 27, 29, 30, 31, 33, 34, 35, 38, 39 and 40) and 7 males and 9 females at 4 months (Nos. 2, 3, 4, 7, 8, 9, 25, 26, 28, 29, 33, 34, 35, 36, 38 and 39) the respective mean pretreatment values: $32.8 \pm 6.5$ ng/ml $14.3 \pm 2.0$ ng/ml; $1.28 \pm 0.18$ U/ml; $4.6 \pm 0.3$ cm/yr and $25.8 \pm 4.8$ ng/ml; $14.0 \pm 2.1$ ng/ml; $1.6 \pm 0.3$ U/ml; $4.8 \pm 0.38$ cm/yr were not significantly altered when evaluated at 2 and 4 months of clonidine treatment.

No significant difference was found, at 2 months in pretreatment values between C-R and C-NR, in the standard deviation score, bone age, ratio bone age, chronological age, peak GH response to acute GHRH or clonidine, SM-C levels, the only difference being an initial GV significantly lower in C-R than in C-NR children ($2.8 \pm 0.2$ and $2.8 \pm 0.25$ cm/yr, vs. $4.6 \pm 0.3$ and $4.8 \pm 0.38$ cm/yr, respectively at 2 and 4 months, $P < 0.01$).

Evaluation of the GV at 4 months showed that 3 females and 2 males (Nos. 3, 9, 25, 28 and 36), who were C-R at 2 months, were now C-NR, while, conversely, 6 males and 1 female (Nos. 6, 13, 22, 27, 30, 31 and 40), C-NR at 2 months, became C-R, so that at 4 months, of the C-R children, 15 were males and 6 females (Table 4). Also at this time interval, the initial GV of the C-R children was significantly lower than that of C-NR children ($2.8 \pm 0.25$ cm/yr vs. $4.8 \pm 0.38$ cm/yr, $P < 0.01$).

TABLE 3

| PATIENT NO. | SEX | CHRONOLOGICAL AGE (yr) | BONE AGE* (yr) | SDS* | PUBERIAL STAGE (TANNER) |
|---|---|---|---|---|---|
| 1 | F | 11.1 | 8.6 | −3.5 | $P_0$ |
| 2 | F | 11.3 | 9.1 | −3.5 | $P_0$ |
| 3 | F | 10.1 | — | −3.8 | $P_0$ |
| 4 | F | 7.2 | 3.2 | −4.8 | $P_0$ |
| 5 | F | 11.2 | 8.6 | −2.9 | $P_0$ |
| 6 | M | 11.6 | 10.1 | −2.0 | $P_0$ |
| 7 | M | 8.2 | 6.6 | −4.1 | $P_0$ |
| 8 | M | 9.1 | 7.3 | −2.8 | $P_0$ |
| 9 | F | 11.3 | 6.4 | −4.6 | $P_0$ |
| 10 | M | 5.1 | — | −1.8 | $P_0$ |
| 11 | M | 14.5 | 10.2 | −3.0 | $P_2$ |
| 12 | M | 8.5 | 7.0 | −2.4 | $P_1$ |
| 13 | M | 12.0 | 9.2 | −4.0 | $P_1$ |
| 14 | M | 7.5 | 5.0 | −3.9 | $P_0$ |
| 15 | M | 8.5 | 6.6 | −1.8 | $P_0$ |
| 16 | M | 15.2 | 11.6 | −5.2 | $P_1$ |
| 17 | F | 5.2 | 4.6 | −2.0 | $P_0$ |
| 18 | F | 15.4 | 12.0 | −2.8 | $P_1$ |
| 19 | F | 7.2 | — | −1.2 | $P_0$ |
| 20 | F | 13.2 | 11.7 | −3.6 | $P_1$ |
| 21 | F | 11.3 | 10.2 | −2.0 | $P_1$ |
| 22 | F | 6.2 | 5.2 | −2.8 | $P_0$ |
| 23 | M | 9.7 | 9.1 | −2.0 | $P_0$ |
| 24 | F | 9.2 | 6.4 | −3.2 | $P_0$ |
| 25 | M | 13.1 | 11.5 | −2.0 | $P_1$ |
| 26 | M | 5.6 | 3.2 | −3.8 | $P_0$ |
| 27 | M | 15.1 | 13.3 | −4.0 | $P_2$ |
| 28 | F | 11.8 | 11.2 | −4.4 | $P_1$ |
| 29 | F | 10.2 | 8.2 | −1.8 | $P_0$ |
| 30 | M | 5.2 | 2.6 | −5.0 | $P_0$ |
| 31 | M | 5.8 | 3.5 | −5.0 | $P_0$ |
| 32 | M | 9.8 | 6.5 | −2.2 | $P_0$ |
| 33 | F | 9.4 | 6.1 | −2.4 | $P_0$ |
| 34 | F | 10.8 | 10.0 | −2.5 | $P_0$ |
| 35 | M | 13.2 | 12.0 | −2.8 | $P_1$ |
| 36 | M | 7.0 | — | −1.8 | $P_0$ |
| 37 | M | 13.3 | 7.6 | −5.0 | $P_1$ |
| 38 | M | 9.8 | 8.6 | −1.8 | $P_0$ |
| 39 | F | 11.7 | 10.2 | −2.0 | $P_0$ |
| 40 | M | 9.6 | 7.2 | −3.0 | $P_0$ |

*SDS, Standard deviation score (number of SD from the mean for age)
*Calculated according to Tanner T.W-2

TABLE 4

| GH C (U/ml) | | | GROWTH VELOCITY (cm/yr) | | | Patient no. | MEAN GH RESPONSE TO GHRH (mg/ml) | | | PEAK GH RESPONSE TO CLONIDINE (mg/ml) | | |
|---|---|---|---|---|---|---|---|---|---|---|---|---|
| Pretreatment | 2 mos. | 4 mos. | Pretreatment | 2 mos. | 4 mos. | | Pretreatment | 2 mos. | 4 mos. | Pretreatment | 2 mos. | 4 mos. |
| 1.24 | 1.4 | 1.74 | 2.0 | 4.0 | 4.2 | 1 | 55.9 | 26.0 | 27.6 | 12.5 | 28.0 | 21.4 |
| 3.96 | 2.2 | 6.7 | 7.5 | 9.6 | 4.2 | 2 | 16.1 | 28.4 | 11.1 | 14.8 | 24.9 | 2.6 |
| 1.25 | 2.7 | 2.7 | 6.0 | 10.0 | 6.0 | 3 | 26.3 | 44.5 | 31.7 | 11.2 | 26.4 | 16.4 |
| 0.5 | 0.7 | 0.7 | 4.2 | 3.8 | 4.2 | 4 | 53.2 | 27.7 | 37.0 | 9.4 | 11.7 | 11.0 |
| 0.9 | 3.2 | 2.0 | 3.1 | 6.7 | 6.4 | 5 | 26.2 | 42.7 | 51.0 | 9.0 | 18.0 | 22.5 |
| 1.7 | 2.4 | 2.04 | 3.5 | 4.5 | 10.0 | 6 | 3.6 | 49.9 | 56.1 | 12.9 | 25.0 | 25.0 |
| 0.9 | 3.0 | 3.2 | 4.5 | 5.0 | 6.0 | 7 | 16.3 | 15.9 | 41.0 | 16.4 | 18.0 | 21.7 |
| 1.0 | 0.9 | 1.94 | 5.0 | 6.0 | 5.8 | 8 | 34.7 | 25.3 | 35.3 | 42.3 | 5.6 | 19.7 |
| 0.54 | 2.2 | 2.6 | 5.0 | 10.0 | 7.4 | 9 | 100.0 | 92.2 | 54.6 | 27.0 | 17.8 | 18.7 |
| 1.0 | 3.6 | 4.01 | 3.5 | 9.0 | 8.0 | 10 | 46.0 | 59.0 | 41.0 | 4.4 | 26.6 | 17.6 |
| 2.16 | 4.2 | 2.05 | 2.5 | 9.0 | 3.2 | 11 | 7.0 | 16.1 | 59.4 | 12.0 | 24.7 | 18.4 |
| 0.84 | 3.0 | 1.98 | 0.6 | 7.2 | 6.0 | 12 | 21.2 | 45.9 | 42.0 | 19.4 | 21.8 | 11.0 |

TABLE 4-continued

| GH C (U/ml) | | | GROWTH VELOCITY (cm/yr) | | | Patient no. | MEAN GH RESPONSE TO GHRH (mg/ml) | | | PEAK GH RESPONSE TO CLONIDINE (mg/ml) | | |
|---|---|---|---|---|---|---|---|---|---|---|---|---|
| Pretreatment | 2 mos. | 4 mos. | Pretreatment | 2 mos. | 4 mos. | | Pretreatment | 2 mos. | 4 mos. | Pretreatment | 2 mos. | 4 mos. |
| 2.02 | 1.4 | 3.07 | 2.7 | 2.6 | 7.3 | 13 | 50.7 | 11.6 | 79.5 | 36.4 | 7.4 | 27.0 |
| — | 1.9 | — | 0.8 | 6.0 | 5.5 | 14 | 19.3 | 44.8 | 22.0 | 5.6 | 11.4 | 15.4 |
| 0.65 | 2.7 | 0.5 | 2.1 | 4.4 | 9.6 | 15 | 19.2 | 28.2 | 40.2 | 4.0 | 16.6 | 19.0 |
| 2.3 | 2.3 | 2.2 | 2.4 | 5.2 | 9.6 | 16 | 0.6 | 42.2 | 14.4 | 14.2 | 31.7 | 32.9 |
| — | 2.94 | 4.8 | 4.0 | 6.7 | — | 17 | 72.0 | 112.2 | — | 36.2 | 92.5 | — |
| 4.48 | 1.92 | — | 3.7 | 6.5 | — | 18 | 32.5 | 42.6 | — | 34.0 | 44.6 | — |
| 0.95 | 0.4 | — | 3.1 | 3.8 | — | 19 | 26.1 | 33.2 | — | 9.2 | 13.7 | — |
| — | 3.1 | 1.9 | 3.8 | 7.6 | 8.2 | 20 | 34.7 | 37.4 | 27.5 | 11.3 | 18.4 | 15.4 |
| 2.3 | 2.95 | 4.0 | 4.2 | 9.0 | 9.0 | 21 | 16.4 | 29.0 | 35.4 | 7.8 | — | 18.7 |
| 1.22 | 1.75 | 1.7 | 3.4 | 5.2 | 6.0 | 22 | 28.6 | 27.4 | 34.7 | 2.7 | — | 14.7 |
| 0.92 | 4.08 | 3.02 | 3.6 | 7.3 | 7.0 | 23 | 5.2 | 24.4 | 58.4 | 5.8 | 23.1 | 21.2 |
| 1.8 | 2.23 | 1.6 | 2.6 | 5.2 | 5.4 | 24 | 22.4 | 27.3 | 43.2 | 3.7 | 12.0 | 12.2 |
| 4.5 | 3.75 | 3.02 | 3.7 | 10.0 | 4.5 | 25 | 3.7 | 11.9 | 9.9 | 12.0 | 11.1 | 6.5 |
| 0.86 | 0.32 | 3.02 | 3.8 | 3.0 | 3.6 | 26 | 22.0 | 32.7 | 21.2 | 14.5 | 11.9 | 7.7 |
| 2.7 | 3.9 | 1.9 | 4.8 | 5.5 | 6.0 | 27 | 21.4 | 52.7 | 72.2 | 5.4 | 27.0 | 28.4 |
| 1.2 | 2.79 | 1.3 | 4.2 | 9.0 | 1.9 | 28 | 4.6 | 32.9 | 7.7 | 6.7 | 18.4 | 5.3 |
| 1.7 | 0.42 | 3.1 | 7.0 | 6.6 | 4.0 | 29 | 19.2 | 7.1 | 16.6 | 18.6 | 11.2 | 10.2 |
| 0.4 | 0.9 | 2.0 | 2.5 | 2.9 | 6.0 | 30 | 149.3 | 39.4 | 28.0 | 28.5 | 32.0 | 20.9 |
| 0.76 | 0.3 | 0.7 | 2.2 | 2.2 | 8.4 | 31 | 50.0 | 52.6 | 60.2 | 7.3 | 45.5 | 44.7 |
| — | 3.25 | 4.07 | 3.5 | 9.0 | 9.0 | 32 | 36.4 | 45.4 | 49.2 | 3.2 | 27.0 | 16.5 |
| 1.2 | 0.7 | 0.4 | 2.7 | 2.8 | 2.0 | 33 | 27.6 | 14.0 | 11.7 | 5.8 | 2.3 | 5.2 |
| 1.4 | 1.9 | 1.06 | 8.0 | 8.0 | 4.5 | 34 | 18.9 | 11.9 | 7.7 | 6.0 | 17.7 | 4.4 |
| 1.04 | 1.0 | 0.4 | 6.0 | 7.9 | 4.8 | 35 | 6.7 | 18.6 | 11.9 | 19.6 | 12.9 | 7.6 |
| 0.4 | 2.85 | 0.5 | 2.4 | 10.8 | 3.0 | 36 | 24.0 | 70.0 | 58.2 | 21.2 | 27.0 | 49.2 |
| 1.76 | 1.6 | 5.4 | 3.8 | 8.6 | 6.0 | 37 | 19.0 | 57.3 | 44.2 | 13.5 | 42.1 | 54.2 |
| — | 0.4 | 1.02 | 4.6 | 4.0 | 3.7 | 38 | 18.7 | 19.0 | 11.7 | 13.5 | 9.4 | 7.6 |
| — | 0.22 | 2.94 | 8.0 | 7.9 | 6.5 | 39 | 18.0 | 12.1 | 49.4 | 10.5 | 10.0 | 27.0 |
| — | 2.3 | 3.86 | 3.0 | 5.7 | 12.0 | 40 | 24.6 | 45.2 | 59.9 | 9.9 | 18.4 | 29.9 |

All the results obtained consequently show that clonidine is able to stimulate the release of GH, increase hypophyseal and plasma levels of this hormone and provoke the biological effects of increased GH secretion (for example linear growth). On the basis of these observations it would appear in conclusion that clonidine is a drug with the ability to cause the release of somatotropic hormone and to stimulate linear growth in children with growth disorders where the main problem lies in the inability of the hypothalamus to release the neurohormone GRF.

Clonidine and the other related 2,6-dichlorophenyl compounds may be administered in the pharmaceutical forms of tablets, drops and syrups for oral use as well as sterile solutions in ampoules for hypodermic or intravenous use. These drugs may also be advantageously administered by transdermal methods with the drug supported on adhesive plasters or dissolved in polymer-based carriers for cutaneous application on specific areas of the body so as to obtain the required release of the most suitable quantities of the drug.

Although the therapeutic applications of clonidine have been illustrated from test data obtained in the area of impaired hypothalamic function leading to growth disorders, clonidine and the other 2,6-dichlorophenyl derivatives mentioned above may be used in the treatment of other hypothalamic-hypophyseal disorders. Clonidine, which is, as mentioned above, able to activate adrenergic neurotransmission in the hypothalamus, could usefully be used for example in the treatment of amenorrhoea having hypothalammic causes. In patients with this syndrome, the amenorrhoeic condition is due to a defective secretion of the hypothalamic nuerohormone LH-RH, which leads, in physiological conditions, to the release of the hypophyseal gonadotropins LH and FSH which are responsible for the maturation of the ovarian follicle and ovulation halfway through the menstrual cycle. The defective secretion of LH-RH prevents ovulation (amenorrhoea) and is responsible for the infertility of such patients.

Since the central adrenergic system plays an important role in the release of LH-RH, as well as in the release of GRF, the prolonged administration of clonidine or its analogues could provide an effective way of inducing ovulation in patients with hypothalamic amenorrhoea.

The same treatment could be envisaged for male patients with idiopathic hypogonadotrophic hypogonadism, with reduced levels of circulating testosterone, hypoazospermia, absence of libido and impotence.

What is claimed is:

1. A method for treating a child with impaired growth caused by hypothalamic abnormality, which comprises administering to such child therapeutically effective amounts of clonidine for a period of at least two months, so as to induce growth.

2. The method of claim 1 wherein the child to be treated suffers from isolated growth hormone deficiency.

3. The method of claim 1 wherein the child to be treated suffers from constitutional growth delay.

4. The method of claim 1 wherein about 0.1 mg/m$^2$ (of body surface) of clonidine is administered orally, daily, for a period of at least about two months.

5. A method for treating a child suffering from impaired growth due to hypothalamic abnormality which comprises orally administering about 0.1 mg/m$^2$ (of body surface) of clonidine per day for a period of at least about two months so as to induce growth.

* * * * *